US012318084B2

(12) United States Patent
Potter, Jr.

(10) Patent No.: US 12,318,084 B2
(45) Date of Patent: Jun. 3, 2025

(54) MEDICAL DEVICES AND METHODS FOR BODY CONDUIT LENGTHENING AND ANASTOMOSIS FORMATION

(71) Applicant: Mayo Foundation for Medical Education and Research, Rochester, MN (US)

(72) Inventor: D. Dean Potter, Jr., Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 17 days.

(21) Appl. No.: 18/221,058

(22) Filed: Jul. 12, 2023

(65) Prior Publication Data

US 2023/0355229 A1 Nov. 9, 2023

Related U.S. Application Data

(62) Division of application No. 16/653,013, filed on Oct. 15, 2019, now Pat. No. 11,737,745.

(60) Provisional application No. 62/749,893, filed on Oct. 24, 2018.

(51) Int. Cl.
*A61B 17/04* (2006.01)
*A61B 17/11* (2006.01)
*A61B 17/34* (2006.01)

(52) U.S. Cl.
CPC ...... *A61B 17/0401* (2013.01); *A61B 17/1114* (2013.01); *A61B 17/3415* (2013.01)

(58) Field of Classification Search
None
See application file for complete search history.

(56) References Cited

U.S. PATENT DOCUMENTS

| | | |
|---|---|---|
| 4,134,405 A | 1/1979 | Smit |
| 4,271,839 A | 6/1981 | Fogarty et al. |
| 4,624,257 A | 11/1986 | Berggren et al. |
| 4,723,547 A | 2/1988 | Kullas et al. |
| 4,964,863 A | 10/1990 | Kanshin et al. |
| 5,092,839 A | 3/1992 | Kipperman |
| 5,141,516 A | 8/1992 | Detweiler |
| 5,282,827 A | 2/1994 | Kensey et al. |
| 5,312,410 A | 5/1994 | Miller et al. |
| 5,411,508 A | 5/1995 | Bessler et al. |
| 5,425,738 A | 6/1995 | Gustafson et al. |
| 5,447,503 A | 9/1995 | Miller |
| 5,486,196 A | 1/1996 | Hirshowitz et al. |
| 5,626,591 A | 5/1997 | Köckerling et al. |
| 5,868,760 A | 2/1999 | McGuckin, Jr. |
| 5,899,882 A | 5/1999 | Waksman et al. |
| 6,063,056 A | 5/2000 | Engelberg |

(Continued)

OTHER PUBLICATIONS

Foker et al., "A flexible approach to achieve a true primary repair of all infants with esophageal atresia," Semin. Pediatr. Surg., Feb. 2005, 14(1):8-15.

(Continued)

*Primary Examiner* — Shaun L David
(74) *Attorney, Agent, or Firm* — Fish & Richardson P.C.

(57) ABSTRACT

Devices and methods for body conduit lengthening and anastomosis creation can be used to treat patients with a variety of health conditions. For example, among other uses, this document describes esophageal lengthening and anastomosis devices that can be used to remedy esophageal atresia in neonatal patients.

11 Claims, 2 Drawing Sheets

(56) References Cited

U.S. PATENT DOCUMENTS

| | | |
|---|---|---|
| 6,251,111 B1 | 6/2001 | Barker et al. |
| 6,689,062 B1 | 2/2004 | Mesallum |
| 6,743,244 B2 | 6/2004 | Blatter et al. |
| 6,869,437 B1 | 3/2005 | Hausen et al. |
| 7,220,268 B2 | 5/2007 | Blatter |
| 7,371,243 B1 | 5/2008 | Nielsen et al. |
| 7,527,590 B2 | 5/2009 | Suzuki et al. |
| 7,892,292 B2 | 2/2011 | Stack et al. |
| 8,083,758 B2 | 12/2011 | Hsu et al. |
| 8,480,694 B2 | 7/2013 | Heinrich et al. |
| 8,821,521 B2 | 9/2014 | Burnett |
| 9,414,878 B1 | 8/2016 | Wu et al. |
| 11,006,958 B2 | 5/2021 | Potter, Jr. |
| 11,737,745 B2 | 8/2023 | Potter, Jr. |
| 2001/0007931 A1 | 7/2001 | Blatter |
| 2002/0185517 A1 | 12/2002 | Vresh et al. |
| 2003/0216613 A1 | 11/2003 | Suzuki et al. |
| 2003/0222117 A1 | 12/2003 | Orban, III |
| 2004/0097973 A1 | 5/2004 | Loshakove et al. |
| 2004/0147801 A1 | 7/2004 | Kugler et al. |
| 2004/0153167 A1 | 8/2004 | Stack et al. |
| 2004/0215233 A1 | 10/2004 | Kaplan et al. |
| 2005/0021053 A1 | 1/2005 | Heinrich |
| 2005/0143766 A1 | 6/2005 | Bachmann et al. |
| 2005/0149071 A1 | 7/2005 | Abbott et al. |
| 2005/0149072 A1 | 7/2005 | DeVries et al. |
| 2005/0182475 A1 | 8/2005 | Jen et al. |
| 2005/0209614 A1 | 9/2005 | Fenter et al. |
| 2006/0079897 A1 | 4/2006 | Harrison et al. |
| 2006/0167474 A1 | 7/2006 | Bloom et al. |
| 2006/0253139 A1 | 11/2006 | Ortiz |
| 2006/0286145 A1 | 12/2006 | Horan et al. |
| 2007/0049954 A1 | 3/2007 | Caty et al. |
| 2007/0073098 A1 | 3/2007 | Lenker et al. |
| 2007/0213582 A1 | 9/2007 | Zollinger et al. |
| 2007/0265643 A1 | 11/2007 | Beane et al. |
| 2008/0015618 A1 | 1/2008 | Sonnenschein et al. |
| 2008/0172087 A1 | 7/2008 | Fuchs et al. |
| 2009/0018604 A1 | 1/2009 | Mitelberg et al. |
| 2009/0048618 A1 | 2/2009 | Harrison et al. |
| 2009/0281557 A1 | 11/2009 | Sander et al. |
| 2010/0121371 A1 | 5/2010 | Brooks et al. |
| 2010/0179510 A1 | 7/2010 | Fox et al. |
| 2010/0222802 A1 | 9/2010 | Gillespie, Jr. et al. |
| 2011/0137325 A1 | 6/2011 | Nolan et al. |
| 2011/0218476 A1 | 9/2011 | Kraemer et al. |
| 2011/0264125 A1 | 10/2011 | Wilson et al. |
| 2011/0288570 A1 | 11/2011 | Copa |
| 2012/0024935 A1 | 2/2012 | Shelton, IV et al. |
| 2012/0035628 A1 | 2/2012 | Aguirre et al. |
| 2012/0204865 A1 | 8/2012 | Filipi et al. |
| 2013/0030351 A1 | 1/2013 | Belhe et al. |
| 2013/0079603 A1 | 3/2013 | Vargas |
| 2013/0226205 A1 | 8/2013 | Zaritsky et al. |
| 2013/0261680 A1 | 10/2013 | Baccell et al. |
| 2013/0274772 A1 | 10/2013 | Kim et al. |
| 2014/0058418 A1 | 2/2014 | Romley |
| 2014/0148828 A1 | 5/2014 | Ewers et al. |
| 2014/0188142 A1 | 7/2014 | Belson |
| 2014/0309634 A1 | 10/2014 | Weisshaupt et al. |
| 2014/0343576 A1 | 11/2014 | Romley |
| 2014/0350566 A1 | 11/2014 | Emmanouilidis |
| 2015/0119877 A1 | 4/2015 | Jameson et al. |
| 2015/0133771 A1 | 5/2015 | Marczyk et al. |
| 2015/0142048 A1 | 5/2015 | Coleman et al. |
| 2015/0342609 A1 | 12/2015 | DuPont et al. |
| 2017/0311952 A1 | 11/2017 | Potter et al. |
| 2017/0360524 A1 | 12/2017 | Peiro Ibanez |
| 2018/0228491 A1 | 8/2018 | Potter |
| 2019/0239887 A1 | 8/2019 | Potter |
| 2020/0129169 A1 | 4/2020 | Potter, Jr. |

OTHER PUBLICATIONS

Harrison, "Presidential Address: What if? . . . Why not?," J. Pediatr. Surg., Jan. 2010, 45(1):1-10.

Hendren et al., "Electromagnetic bougienage to lengthen esophageal segments in congenital esophageal atresia," N. Engl. J. Med., Aug. 1975, 293(9):428-432.

Jamshidi et al., "Magnamosis: magnetic compression anastomosis with comparison to suture and staple techniques," J. Pediatr. Surg., Jan. 2009, 44(1):222-228.

Pichakron et al., "Magnamosis II: Magnetic compression anastomosis for minimally invasive gastrjejunostomy and jejunojejunostomy," J. Am. Coll. Surg, Jan. 2011, 212(1):42-49.

Potter, "Esophageal Atresia Repair Device," Mayo Clinic ©, 2016, 1 page.

Zaritzky et al., "Magnetic compression anastomosis as a nonsurgical treatment for esophageal atresia," Pediatr. Radiol., Sep. 2009, 39(9):945-949.

U.S. Appl. No. 15/493,947, filed Apr. 21, 2017, D. Dean Potter Jr., Issued as U.S. Pat. No. 10,299,795.

U.S. Appl. No. 16/382,711, filed Apr. 12, 2019, D. Dean Potter Jr., Issued as U.S. Pat. No. 11,006,958.

MEDICAL DEVICES AND METHODS FOR BODY CONDUIT LENGTHENING AND ANASTOMOSIS FORMATION

CROSS-REFERENCE TO RELATED APPLICATIONS

This application is a Divisional of U.S. Utility application Ser. No. 16/653,013, filed Oct. 15, 2019, which claims the benefit of U.S. Provisional Application Ser. No. 62/749,893, filed Oct. 24, 2018. The disclosures of the prior applications are considered part of (and are incorporated by reference in) the disclosure of this application.

BACKGROUND

1. Technical Field

This document relates to devices for body conduit lengthening and anastomosis creation, and methods for their use. For example, among other uses, this document relates to esophageal lengthening and anastomosis devices that can be used to remedy esophageal atresia in neonatal patients. In addition, the devices and methods provided herein can also be used to treat other body lumens and conduits such as, but not limited to, blood veins, arteries, fallopian tubes, urethrae, ureters, and the like.

2. Background Information

Esophageal atresia (EA) is a birth defect in which the esophagus does not extend continuously into the stomach. Rather, the esophagus exists as two separate tubes; one originating from the mouth and the other ending in the stomach. It affects about one out of every 3,500 infants in the United States. The most common form of the condition is EA with a tracheoesophageal fistula (TEF) in which the lower portion of the esophagus joins with the trachea. This occurs in approximately 85% of patients. The next most common form (~10%) is pure EA in which no portion of the esophagus joins with the trachea.

Current treatment of EA with TEF, the most common form of EA, involves either a thoracotomy or minimally invasive thoracic surgery where the lower esophagus is separated from the trachea. Routinely, an anastomosis of the two esophageal ends then follows, requiring the intricate task of suturing the esophageal pouches together. The procedure has a very high success rate but is fraught with a number of complications; anastomotic leak in 10%, anastomotic stricture in 10-20%, and gastroesophageal reflux disease or severe motility dysfunction in up to 50% of patients, to name a few. These complications are believed to be caused by the tension required to re-approximate the esophageal ends for anastomosis.

Pure EA, on the other hand, cannot currently be repaired with a single procedure. That is the case because the esophagus ends are too far apart to be brought together. For example, the gap between the esophageal ends can be as long as 8 cm. Instead, typical treatment involves waiting for the esophagus to grow on its own until the ends are close together, at which point the segments can be connected. Though this process sounds reasonably straightforward, the waiting can take three to six months, and requires the infant to have a gastrostomy tube for feeding during that time. This technique is prone to the same complications mentioned above because the esophagus is, once again, under tension when repaired. Additionally, it has been shown the anastomotic leak rate and stricture formation are even higher for pure EA, due to the excessive tension required to bring the esophageal ends together.

SUMMARY

This document describes devices for body conduit lengthening and anastomosis creation, and methods for their use. For example, among other uses, this document describes esophageal lengthening and anastomosis devices that can be used to remedy esophageal atresia in neonatal patients. In additional examples, the devices and methods provided herein can also be used to treat other body lumens and conduits such as, but not limited to, blood veins, arteries, fallopian tubes, urethrae, ureters, and the like. The devices and method can also be used for a variety of other medical treatments such as, but not limited to, repair of duodenal atresia, multiple types of natural orifice transesophageal surgery anastomoses, endoscopic stricturoplasty of various body conduits, and creation of ileal pouch anal anastomosis.

In one aspect, this disclosure is directed to a body conduit lengthening and anastomosis device. Such a body conduit lengthening and anastomosis device includes: (i) a tensioning assembly including a tension sensor coupled to a motor; (ii) an extension sheath coupled to and extending distally from the tensioning assembly, the extension sheath defining an extension sheath lumen therethrough; (iii) a catheter coupled to the tension sensor, the catheter slidably disposed within the extension sheath lumen; (iv) a flexible sheath extending distally from the extension sheath and defining a flexible sheath lumen therethrough, the catheter slidably disposed within the flexible sheath lumen; and (v) an inflatable balloon member disposed at a distal end portion of the catheter. In some embodiments, the tensioning assembly is configured to pull the catheter proximally in relation to the flexible sheath when the motor is actuated.

Such a body conduit lengthening and anastomosis device may optionally include one or more of the following features. The flexible sheath may include a distal tip. An interference fit may exist between the distal tip and the balloon member while the balloon member is inflated, and/or a clearance fit may exist between the distal tip and the balloon member while the balloon member is deflated. The distal tip may be reconfigurable between a low-profile diametrically collapsed configuration and a diametrically expanded configuration. The device may also include a controller in electrical communication with the tension sensor and the motor. The controller may be configured to receive a tension set-point and to control the motor so that the catheter is tensioned at the tension set-point. The catheter may define a catheter lumen configured to slidably receive a guidewire. The balloon member may be cylindrical while the balloon member is inflated.

In another aspect, this disclosure is directed to a method of lengthening two body conduits and creating an anastomosis between the two body conduits. Such a method includes: (a) advancing a sheath defining a lumen in which a balloon catheter is slidably disposed into a first body conduit so that a distal end portion of the sheath abuts a wall of the first body conduit; (b) passing a distal end portion of the balloon catheter through the wall of the first body conduit; (c) passing the distal end portion of the balloon catheter through a wall of a second body conduit, wherein the distal end portion of the balloon catheter includes a balloon member; (d) inflating the balloon member while the balloon member is residing in the second body conduit; (e) exerting, using a motor, a tension on the balloon catheter in relation to the sheath so that the wall of the first body conduit and the wall of the second body conduit are drawn closer to each other; and (f) detecting, using a tension sensor, the tension exerted by the motor on the balloon catheter.

Such a method of lengthening two body conduits and creating an anastomosis between the two body conduits may optionally include one or more of the following features. The method may also include using a controller that is in electrical communication with the motor and the tension sensor to control the tension exerted by the motor to a consistent set-point. The method may also include using a controller that is in electrical communication with the motor and the tension sensor to control the tension exerted by the motor in accordance with a predetermined pattern. The method may also include allowing a first period of time to pass while the tension is being exerted, wherein the tension draws the wall of the first body conduit and the wall of the second body conduit closer to each other. The method may also include allowing a second period of time to pass while the tension is being exerted, wherein the wall of the first body conduit and the wall of the second body conduit are in contact with each other after the second period of time. The method may also include allowing a third period of time to pass while the third tension is being exerted, wherein after the third period of time an anastomosis is created between the first body conduit and the second body conduit. In some embodiments, the body conduits are blood vessels. In some embodiments, the body conduits are urogenital conduits. In some embodiments, the body conduits are fallopian tubes. In some embodiments, the body conduits are gastrointestinal conduits.

Particular embodiments of the subject matter described in this document can be implemented to realize one or more of the following advantages. First, only one operation is required to place the device and connect the body conduit ends, whereas previous techniques tend to require at a minimum two operations. Second, by inducing growth of the body conduit ends by tension, the number of anastomotic leaks and strictures will likely decrease. Third, the length of hospitalization, the potential for trauma and complications, and cost of care of these complex patients will likely be reduced. Fourth, in the case of pure EA, the prolonged treatment time of three to six months for the conventional technique brings with it abundant hurdles to overcome. These infants require suctioning of the saliva that accumulates in the upper esophageal pouch. Despite this removal, many of the infants still develop chronic lung disease as a result of the aspiration of their own saliva. Additionally, these children have never consumed nutrition by mouth due to the esophageal obstruction, thus they develop oral aversion. This problem does resolve; however, retraining to eat can take years. Though one could wait longer for the esophagus to grow such that no tension is present when it is connected, it is critical that the esophagus be connected as soon as possible to hopefully lessen the severity of chronic lung disease and oral aversion. To that end, the devices and methods provided herein can reduce the treatment time to several weeks in infants with pure EA, and in other similar cases. Fifth, intestinal anastomoses created using natural orifice transesophageal surgery as described herein obviates the need for abdominal incisions, thus reducing pain, incisional hernia formation and hospital stays. Sixth, endoluminal resection of intestinal strictures using the devices described herein can reduce the number of repeated dilations or surgical interventions needed to treat these lesions. Seventh, some embodiments of the body conduit lengthening and anastomosis devices described herein include one or more sensors that detect and measure the amount of tensile force that is applied by the device to the body conduits. Such force measurements can be used as feedback for closed-loop control of the tensile force. Eighth, in some embodiments patterns of tensile force modulation can be applied to enhance the treatment effects.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document describes devices for body conduit lengthening and anastomosis creation, and methods for their use. For example, among other uses, this document describes esophageal lengthening and anastomosis devices that can be used to remedy esophageal atresia in neonatal patients. While the examples and description provided herein are generally in the context of treatment of long gap EA, it should be understood that the devices and methods can also be similarly used for a variety of other medical treatments such as, but not limited to, repair of duodenal atresia, multiple types of natural orifice transesophageal surgery anastomoses, endoscopic stricturoplasty of various body conduits, and creation of ileal pouch anal anastomosis. Moreover, the devices and methods provided herein can also be used to similarly treat other body lumen and conduits such as, but not limited to, blood veins, arteries, fallopian tubes, urethrae, ureters, and the like.

In one non-limiting example, this disclosure provides devices and methods to treat long gap EA, while obviating much of the delay and complexities associated with current procedures. The devices and methods provided herein involve actively stretching the body conduit, e.g., esophagus portions, with traction to promote growth of the esophagus portions. Moreover, the devices and methods provided herein allow for a compression anastomosis to occur between the body conduit ends, e.g., esophageal ends. This eliminates the need for a second operation to suture the body conduit, e.g., esophageal ends together.

In the exemplary context of treatment of long gap EA, the anastomotic devices provided herein use an oroesophageal tube that is passed through the baby's mouth to apply pressure on the upper esophageal segment. A balloon tipped catheter is passed via the tube through the upper esophageal segment and into the lower esophageal segment. Once the balloon is inflated and secured, traction is applied between the esophageal ends over a period of several days. Once the esophageal ends have grown together, the balloon and oroesophageal tube will unite to create a compression anastomosis between the two esophageal ends. After formation of the tissue anastomosis, the device would then be ready to slip out of the patient's mouth.

In this context, compression anastomosis involves connecting two bowel segments by axially compressing the two ends together and holding them in place to create an internal tissue-growth connection. That is, the two ends will fuse together creating a natural anastomosis while the superfluous flesh loses blood supply and auto-amputates.

Figure 1:
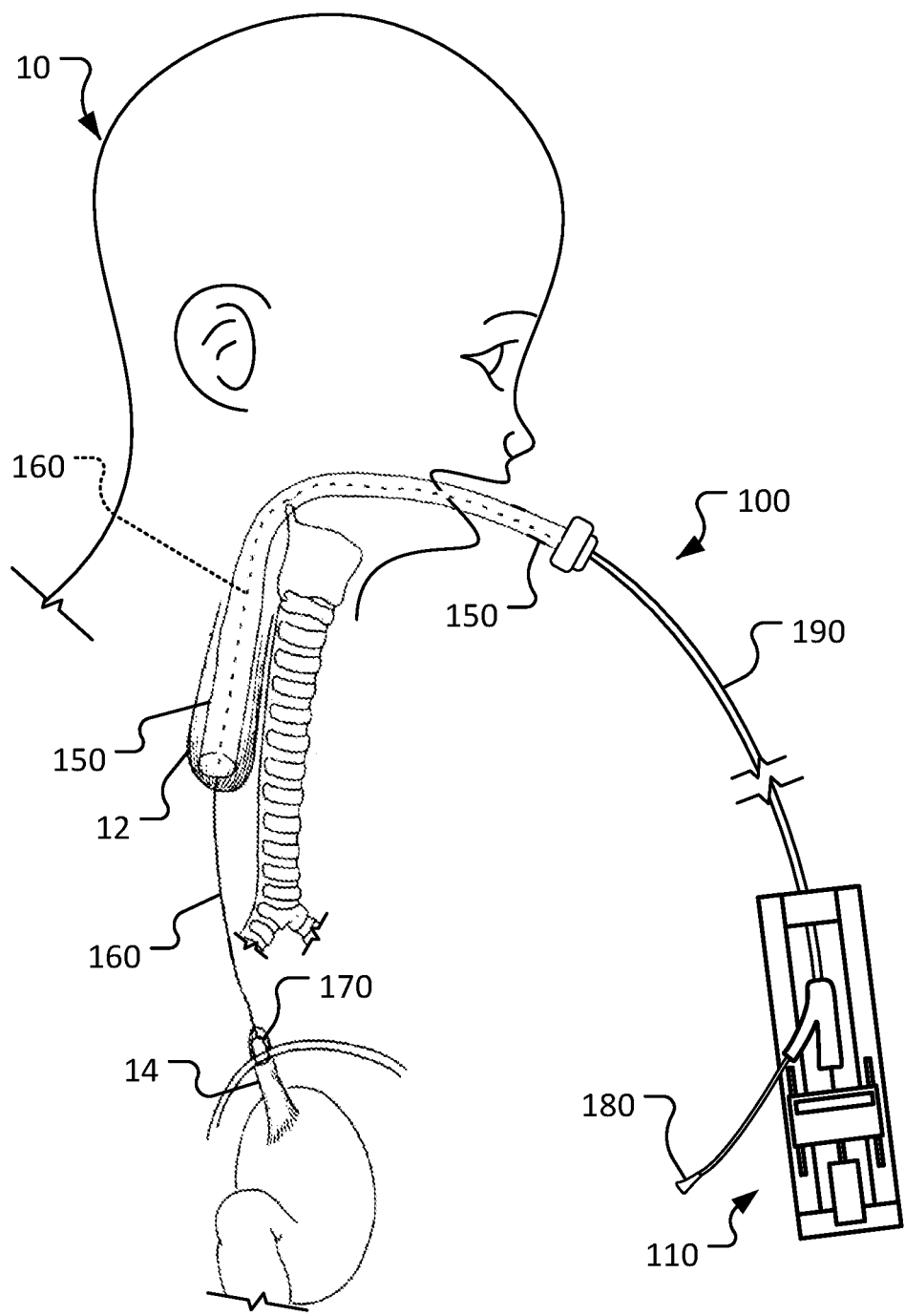
FIG. 1 is a schematic diagram of patient undergoing an esophageal lengthening treatment using a body conduit lengthening and anastomosis device in accordance with some embodiments provided herein.

Again, it should be understood that the devices and methods described herein can be used to treat various conditions involving lengthening body conduits and/or creating anastomoses between body conduits, such as but not limited to:
1. Open, thoracoscopic or endoscopic repair of esophageal atresia.
2. Open, laparoscopic or endoscopic repair of duodenal atresia.
3. Natural orifice transesophageal surgery (NOTES) anastomoses including
   a. Gastrojejunostomy
   b. Duodenojejunostomy
   c. Cystogastrostomy
   d. Jejunocholecystostomy
   e. Ileocolostomy
   f. Jejunocolostomy
4. Endoscopic stricturoplasty of esophagus, colon, rectum or duodenum.
5. Open, laparoscopic or endoscopic creation of ileal pouch anal anastomosis, particularly under tension.
6. Open, thoracoscopic or endoscopic treatments to lengthen and/or create anastomoses between body conduits such as:
   a. blood veins
   b. arteries
   c. fallopian tubes
   d. urethrae
   e. ureters
   f. other body conduits and/or lumens Referring to the example of FIG. 1, an infant patient 10 is receiving treatment for EA using an example body conduit lengthening and anastomosis device 100. In this example, the treatment includes the application of traction between: (a) a first esophageal segment 12 that extends from the mouth of patient 10 and (b) a second esophageal segment 14 that extends from the stomach of the patient 10. As described further below, the traction force is exerted by body conduit lengthening and anastomosis device 100. It should be understood that the devices described herein can be similarly used to exert traction forces to other body conduits such as, but not limited to, blood veins, arteries, fallopian tubes, urethrae, ureters, and the like.

Over time, the traction force exerted by body conduit lengthening and anastomosis device 100 will cause the terminal ends of first esophageal segment 12 and second esophageal segment 14 to become closer together. In some cases, body conduit lengthening and anastomosis device 100 autonomously applies generally constant tension (traction force) as the terminal ends of first esophageal segment 12 and second esophageal segment 14 become closer together. In some cases, at one or more occasions during that time, a clinician may adjust body conduit lengthening and anastomosis device 100 to continue the exertion of a desired level of traction force as the terminal ends of first esophageal segment 12 and second esophageal segment 14 become closer together.

Eventually, the terminal ends of first esophageal segment 12 and second esophageal segment 14 will reach each other, and will become approximated with each other. At that stage of the treatment, body conduit lengthening and anastomosis device 100 will help cause the creation of a compression anastomosis between first esophageal segment 12 and second esophageal segment 14. After formation of the anastomosis, the esophagus of patient 10 will be a patent conduit extending from the mouth to the stomach, which is the intended result of the treatment. Hence, body conduit lengthening and anastomosis device 100 facilitates: (i) lengthening of body conduits, e.g., esophageal segments 12 and 14, and (ii) the creation of a tissue anastomosis between body conduits, e.g., esophageal segments 12 and 14. It should be understood that body conduit lengthening and anastomosis creation can also be facilitated by the devices provided herein for other body conduits such as blood veins, arteries, fallopian tubes, urethrae, ureters, and the like.

Example body conduit lengthening and anastomosis device 100 includes a tensioning assembly 110, a flexible sheath 150, a catheter 160, an inflatable balloon member 170, a balloon inflation tube 180, and a proximal extension sheath 190. Flexible sheath 150 extends distally from proximal extension sheath 190. Tensioning assembly 110 is releasably attached to a proximal end portion of proximal extension sheath 190. In some embodiments, tensioning assembly 110 can be attached at various positions along the length of proximal extension sheath 190 to accommodate adjustments over time during a body conduit lengthening and anastomosis formation procedure. In some embodiments, tensioning assembly 110 is coupled directly to flexible sheath 150. In some embodiments, tensioning assembly 110 is releasably coupled to flexible sheath 150.

Flexible sheath 150 defines a lumen extending longitudinally along the length of flexible sheath 150. In use, flexible sheath 150 can extend out of the mouth of patient 10, but in some embodiments is small enough to reside internally, that is, within the esophageal segment 12 or partially within the esophageal segment 12 and partially within the oral cavity. Accordingly, in some such embodiments proximal extension sheath 190 extends out of the mouth of patient 10.

In some embodiments, body conduit lengthening and anastomosis device 100 includes additional components, for suction (e.g., to remove saliva or stomach contents), irrigation, medication administration, tube feeding, etc.

Catheter 160 extends distally from tensioning assembly 110 and passes through the lumens of proximal extension sheath 190 and flexible sheath 150. Inflatable balloon member 170 is coupled to a distal end portion of catheter 160. Inflatable balloon member 170 is expandable and retractable in response to the supply of an inflation fluid and the withdrawal of the inflation fluid respectively via balloon inflation tube 180. Catheter 160 includes an inflation fluid lumen along a length of catheter 160. The inflation fluid lumen is in fluid communication with inflatable balloon member 170 and balloon inflation tube 180.

The body conduit lengthening and anastomosis device 100 may be put into the depicted operative arrangement in relation to patient 10 using various suitable medical techniques. For example, thoracoscopic and/or endoscopic surgical techniques are used in some cases. Moreover, imaging techniques such as fluoroscopy and/or ultrasound are used in some cases.

While balloon member 170 is in its deflated configuration, the distal end portion of catheter 160 is passed through the terminal ends of both esophageal segments 12 and 14. Thereafter, while inflatable balloon member 170 is within second esophageal segment 14, inflatable balloon member 170 is inflated. In some cases, reinforcement (e.g., one or more sutures, clips, pledgets, etc.) may be added to the terminal end of first esophageal segment 12 and/or second esophageal segment 14.

In the depicted operative arrangement, a distal end portion of sheath 150 abuts the terminal end of first esophageal segment 12, and inflatable balloon member 170 (in its inflated configuration) abuts the terminal end of second esophageal segment 14. Tensioning assembly 110 can then be used to pull (exert traction force) catheter 160 proximally, while maintaining the position of sheath 150 stationary (in relation to tensioning assembly 110). Accordingly, as a result of the traction force, the terminal ends of first esophageal segment 12 and second esophageal segment 14 will be drawn closer together along the axis of catheter 160.

Over a period of time, esophageal segments 12 and 14 will become lengthened. During that time, the traction force exerted by tensioning assembly 110 (and sheath 150 and balloon member 170) can be adjusted one or more times (either manually or automatically). Such adjustments involve changing the relative position of catheter 160 with respect to tensioning assembly 110. That is, to add traction force, the catheter 160 is moved proximally in relation to tensioning assembly 110. As described further below, tensioning assembly 110 has one or more mechanism for facilitating such relative movements/adjustments. In some embodiments, the force between esophageal segments 12 and 14 is held substantially constant while the tensioning assembly 110 is adjusting continuously over the duration of the 1-3 week procedure.

Figure 2:
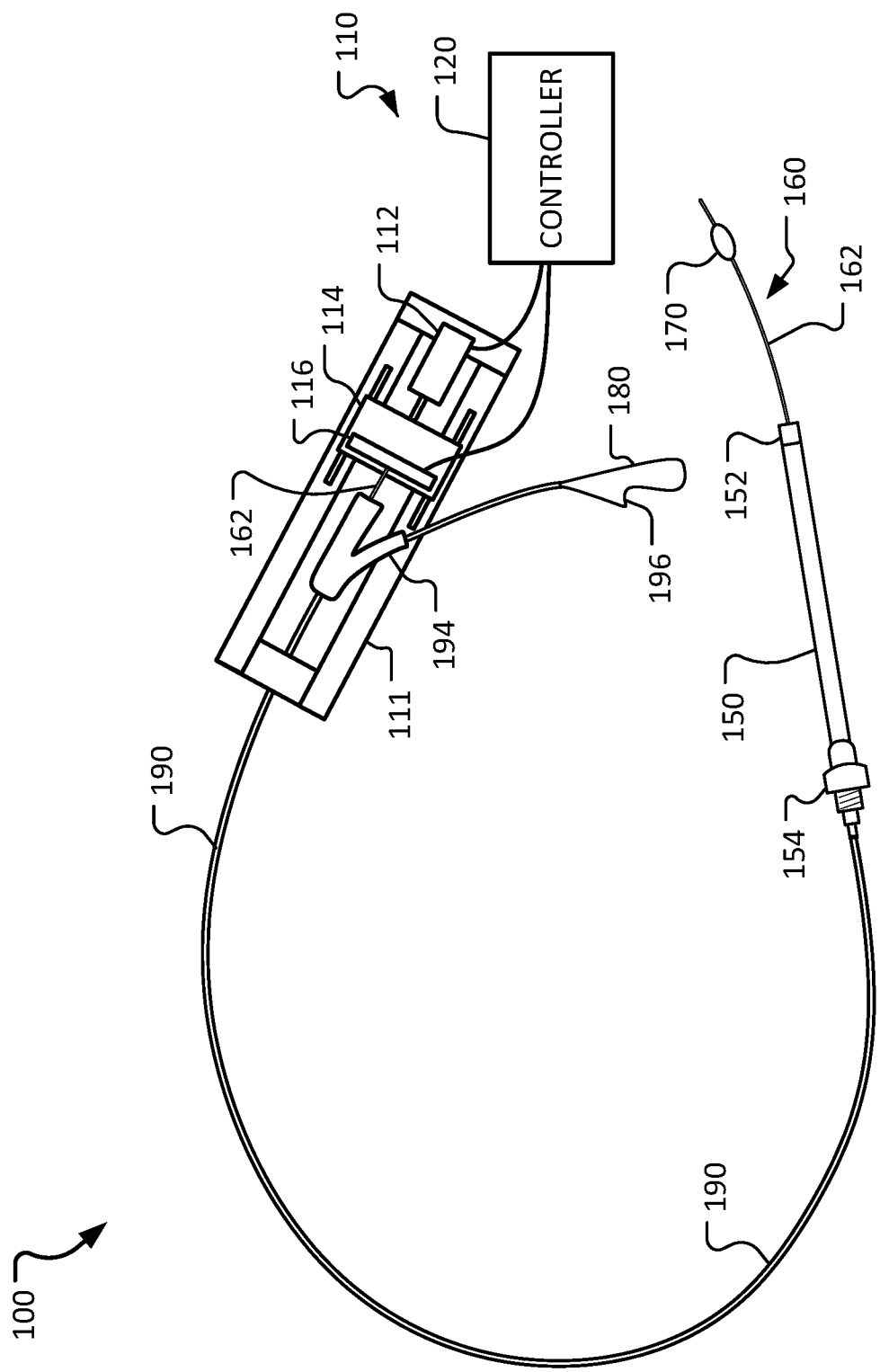
FIG. 2 illustrates an example body conduit lengthening and anastomosis device in accordance with some embodiments provided herein.

Referring also to FIG. 2, a first example embodiment of body conduit lengthening and anastomosis device 100 is depicted in greater detail. In the depicted embodiment, body conduit lengthening and anastomosis device 100 includes tensioning assembly 110, flexible sheath 150, catheter 160, inflatable balloon member 170, balloon inflation tube 180, and proximal extension sheath 190. Additional design embodiments of body conduit lengthening and anastomosis device 100 are also envisioned using a variety of similarly functioning components.

Flexible sheath 150 can be a tubular member such as a nasogastric (NG) tube and the like, for example. Flexible sheath 150 can be made to have any suitable length. Flexible sheath 150 can be made from any suitable material such as, but not limited to, PEBEX, PICOFLEX, PTFE, ePTFE, FEP, PEEK, silicone, PVC, urethane, polyethylene, polypropylene, and the like, and combinations thereof.

In some embodiments, flexible sheath 150 includes an adjunct end cap member 152 at the distal end of flexible sheath 150. In some embodiments, end cap member 152 makes the distal tip of flexible sheath 150 more atraumatic (e.g., so that sheath 150 does not puncture through the terminal end of first esophageal segment 12). Additionally, end cap member 152 can be configured with a design that is complementary with inflatable balloon member 170 for creation of a compression anastomosis. In some embodiments, end cap member 152 may have a rounded, wedged, and/or gradient configuration that is most amenable to anastomosis formation. In some embodiments, end cap member 152 includes one or more radiopaque (RO) markers.

In some embodiments, end cap member 152 is selectively diametrically expandable and collapsible. Accordingly, during insertion in a patient, end cap member 152 can be diametrically collapsed so as to be less traumatic to the patient. Once in position within the patient's body conduit, end cap member 152 can be diametrically expanded to its full size for creating a compression anastomosis in conjunction with balloon member 170.

In some embodiments, a releasable connector 154 is used to conjoin proximal extension sheath 190 and flexible sheath 150. In some embodiments, no such connector is used and proximal extension sheath 190 is attached or connected directly to flexible sheath 150.

Catheter 160 includes a catheter shaft 162. Catheter shaft 162 can be made from any suitable material such as, but not limited to, PEBEX, PICOFLEX, PTFE, ePTFE, FEP, PEEK, silicone, PVC, urethane, polyethylene, polypropylene, and the like, and combinations thereof. Catheter shaft 162 defines an inflation lumen for conveyance of inflation media from balloon inflation tube 180 to inflatable balloon member 170. In some embodiments, catheter shaft 162 also defines another lumen for slidably receiving a guidewire. That is, in some embodiments catheter 160 can be configured for deployment using an over-the-wire or a rail technique using a guidewire, and/or to facilitate introduction of other tools, medications or feeding. In some embodiments, the distal tip of catheter shaft 162 extends distally beyond inflatable balloon member 170. In some such cases, the distal tip of catheter shaft 162 is configured for piercing tissue (e.g., with a pointed or beveled tip). Catheter shaft 162 may include one or more RO markers at various locations.

Inflatable balloon member 170 is coupled to a distal end portion of catheter shaft 162. In some embodiments, inflatable balloon member 170 is a high-pressure, non-elastic dilatation or angioplasty-type balloon (e.g., made of nylon, PET, PVC, PE, polyurethane, and the like). In some embodiments, inflatable balloon member 170 is a low-pressure, elastomeric balloon (e.g., made of latex, silicone, and the like). Inflatable balloon member 170 can have various shapes. For example, inflatable balloon member 170 can be cylindrical (as shown), spherical, square, tapered, stepped, dog bone, offset, and the like. One or more of the ends of inflatable balloon member 170 can be conical (as shown), radiused, square, spherical, and the like. Inflatable balloon member 170 may include one or more RO markers at various locations. In some embodiments, more than one inflatable balloon member 170 may be included.

In some embodiments, to facilitate the compression anastomosis formation process, an interference fit exists between the outer diameter of the inflatable balloon member 170 (while in its inflated configuration) and an inner diameter of end cap member 152. Alternatively, in some embodiments to facilitate the compression anastomosis formation process, a clearance fit or a line-to-line fit exists between the outer diameter of the inflatable balloon member 170 (while in its inflated configuration) and an inner diameter of end cap member 152.

Proximal extension sheath 190 can be a tubular member, for example. Proximal extension sheath 190 can be made from any suitable material such as, but not limited to, PEBEX, PICOFLEX, PTFE, ePTFE, FEP, PEEK, silicone, PVC, urethane, polyethylene, polypropylene, and the like, and combinations thereof. Proximal extension sheath 190 extends between tensioning assembly 110 and flexible sheath 150. In some embodiments, proximal extension sheath 190 is releasably coupled to either or both of tensioning assembly 110 and flexible sheath 150. Catheter shaft 162 is slidably disposed within a lumen defined by proximal extension sheath 190. Proximal extension sheath 190 can be any suitable length.

In the depicted embodiment, tensioning assembly 110 includes a frame 111, a motor 112, a carriage 114, a tension sensor 116, and a controller 120. Frame 111 can be adjustably attached at various positions along proximal extension sheath 190 (or flexible sheath 150). In the depicted embodiment, a Y-fitting 194 provides access for inflation balloon inflation tube 180 and a guidewire insertion tube 196 to join with proximal extension sheath 190.

Motor 112 is attached to frame 111 and to carriage 114. Carriage 114 is movably attached to frame 111. Accordingly, actuation of motor 112 causes movement of carriage 114 in relation to frame 111. In the depicted embodiment, carriage 114 can translate proximally and distally in relation to frame 111.

Catheter shaft 162 is attached to tension sensor 116, and tension sensor 116 is attached to carriage 114. Accordingly, actuation of motor 112 causes movement of: (i) carriage 114 in relation to frame 111, (ii) tension sensor 116 in relation to frame 111, and (iii) catheter shaft 162 in relation to frame 111. Since frame 111 is held stationary in relation to proximal extension sheath 190 (or flexible sheath 150), actuation of motor 112 also causes movement of catheter shaft 162 in relation to flexible sheath 150. In that manner, balloon member 170 can be drawn proximally toward the distal end portion of flexible sheath 150, to draw the terminal ends of esophageal segments 12 and 14 closer to each other and to create an anastomosis there between as described above in reference to FIG. 1.

Tension sensor 116 is arranged to detect the tension being applied to catheter shaft 162 by motor 112 (via carriage 114). Tension sensor 116 can be any suitable type of device such as, but not limited to, a strain gauge, a spring-based sensor, a load cell, a piezo-resistive load cell, an optical-based sensor, and the like.

Controller 120 receives a signal from tension sensor 116 that is indicative of the tension being applied to catheter shaft 162. Moreover, controller 120 outputs signals to actuate and control motor 112.

In some embodiments, controller 120 includes a user interface whereby a tension setting or set-point can be input. For example, in some embodiments a user may input to controller 120 a desired consistent level of tensile force that will cause the lengthening and/or anastomosis of esophageal segments 12 and 14 in a desired manner. In some such embodiments, during operation, controller 120 will receive from tension sensor 116 signals indicating the tensile force being applied, and then control motor 112 so that the tensile force approximates or matches the tension set-point in a closed-loop fashion.

In some embodiments, a fluctuating level of tensile force may be desired (rather than an always consistent level of tensile force). For example, during the esophageal lengthening process, a pattern of alternating periods of high tensile force and low tensile force may be effective in some circumstances. Such an alternating pattern may be beneficial because ischemia of esophageal segments 12 and 14 may be induced during tensioning, and relaxing the tension can allow for re-profusion of esophageal segments 12 and 14. In some cases, a gradually increasing level of tensile force may be effective. All such possibilities for controlling the application of tensile force according to a pattern or tension algorithm can be accommodated using controller 120 in conjunction with tension sensor 116 and motor 112.

In some embodiments, distance control can be used as an alternative to, or in addition to, tension control. To facilitate distance control, one or more sensors can be used to detect/measure the distance between carriage 114 and motor 112, for example. In some embodiments, frame 111 includes one or more visual marks or indices that can be used to ascertain the position of carriage 114 relative to frame 111. Accordingly, the progress of lengthening body conduits can be tracked in some such cases.

In some embodiments, body conduit lengthening and anastomosis device 100 includes additional ports and/or components, for suction (e.g., to remove saliva or stomach contents), irrigation, medication administration, tube feeding, etc.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A body conduit lengthening and anastomosis creation device, comprising:
   a tensioning assembly including a tension sensor coupled to a motor;
   an extension sheath releasably coupled to and extending distally from the tensioning assembly, the extension sheath defining an extension sheath lumen therethrough;

a catheter coupled to the tension sensor, the catheter slidably disposed within the extension sheath lumen and defining an inflation lumen;

a flexible sheath having a proximal end portion that is releasably connected to a distal end portion of the extension sheath, the flexible sheath defining a flexible sheath lumen therethrough that is in fluid communication with the extension sheath lumen, the catheter slidably disposed within the flexible sheath lumen; and an inflatable balloon member attached to a distal end portion of the catheter and in fluid communication with the inflation lumen of the catheter, wherein the tensioning assembly is configured to pull the catheter proximally in relation to the flexible sheath when the motor is actuated.

2. The device of claim 1, wherein the flexible sheath includes a distal tip, wherein an interference fit exists between the distal tip and the balloon member while the balloon member is inflated, and wherein a clearance fit exists between the distal tip and the balloon member while the balloon member is deflated.

3. The device of claim 2, wherein the distal tip is reconfigurable between a low-profile diametrically collapsed configuration and a diametrically expanded configuration.

4. The device of claim 1, further comprising a controller in electrical communication with the tension sensor and the motor, wherein the controller is configured to receive a tension set-point and to control the motor so that the catheter is tensioned at the tension set-point.

5. The device of claim 1, wherein the catheter defines a catheter lumen configured to slidably receive a guidewire.

6. The device of claim 1, wherein the balloon member is cylindrical while the balloon member is inflated.

7. The device of claim 1, wherein the tensioning assembly further comprises a frame and a carriage that is movably attached to the frame.

8. The device of claim 7, wherein the tension sensor is attached to the carriage.

9. The device of claim 1, further comprising a controller in signal communication with the tension sensor and the motor.

10. The device of claim 9, wherein the controller is configured to output signals to control the motor, wherein the signals are based on: (i) a user defined tension setting and (ii) tension signals received from the tension sensor.

11. The device of claim 9, wherein the controller is configured to output signals to control the motor, and wherein the signals comprise a pattern of alternating periods of high tensile force and low tensile force.

* * * * *